United States Patent
Bühring

(10) Patent No.: US 8,365,581 B2
(45) Date of Patent: Feb. 5, 2013

(54) VALVE FOR A LEAK DETECTOR

(75) Inventor: Heiko Bühring, Oldenburg (DE)

(73) Assignee: Airbus Operations GmbH (DE)

( * ) Notice: Subject to any disclaimer, the term of this patent is extended or adjusted under 35 U.S.C. 154(b) by 0 days.

(21) Appl. No.: 13/041,788

(22) Filed: Mar. 7, 2011

(65) Prior Publication Data

US 2011/0155933 A1 Jun. 30, 2011

Related U.S. Application Data

(63) Continuation of application No. 12/083,759, filed as application No. PCT/EP2006/009822 on Oct. 11, 2006, now Pat. No. 7,921,694.

(30) Foreign Application Priority Data

Oct. 12, 2005 (DE) .......................... 10 2005 048 726

(51) Int. Cl.
*G01M 3/40* (2006.01)
*G01M 3/38* (2006.01)

(52) U.S. Cl. ........................... 73/40.5 R; 73/40; 73/49.5

(58) Field of Classification Search .............. 73/40–49.8
See application file for complete search history.

(56) References Cited

U.S. PATENT DOCUMENTS

| 4,039,938 A | 8/1977 | Link |
| 4,655,607 A | 4/1987 | Kern et al. |
| 4,747,309 A | 5/1988 | Weir |
| RE33,649 E * | 7/1991 | Kawai ........................... 137/554 |
| 5,639,958 A * | 6/1997 | Lange ........................ 73/40.5 A |
| 6,008,658 A | 12/1999 | Suyama et al. |
| 6,112,580 A | 9/2000 | Hesky |
| 6,138,512 A | 10/2000 | Roberts et al. |
| 6,430,988 B1 | 8/2002 | Watanabe |
| 2004/0261538 A1 | 12/2004 | Arscott |
| 2005/0166666 A1 | 8/2005 | Tsukagoshi |
| 2006/0042712 A1 | 3/2006 | Iio et al. |

FOREIGN PATENT DOCUMENTS

| CA | 2648968 A1 | 7/2005 |
| CN | 1293366 A | 5/2001 |
| DE | 1 959 840 A | 6/1971 |
| DE | 2932088 A1 | 2/1981 |
| DE | 19757581 A1 | 7/1998 |
| EP | 0 745 841 A1 | 12/1996 |
| GB | 760791 A | 11/1956 |
| GB | 2057084 A | 3/1981 |
| JP | 60098276 A | 6/1985 |
| JP | 61-120035 A | 6/1986 |
| JP | 4-309832 | 11/1992 |
| JP | 5177382 A | 7/1993 |
| JP | 08166228 A | 6/1996 |
| JP | 09033378 A | 2/1997 |
| JP | 09033379 A | 2/1997 |
| JP | 09061377 A | 3/1997 |
| JP | 2000214042 A | 8/2000 |

(Continued)

OTHER PUBLICATIONS

Japanese Action summary for counterpart Application No. 2008-534928, dated Nov. 8, 2011, with English translation.

*Primary Examiner* — David Rogers
(74) *Attorney, Agent, or Firm* — Lerner, David, Littenberg, Krumholz & Mentlik, LLP

(57) ABSTRACT

A leak detector for detecting a leak in a line includes a transmitting device for generating radiation to be coupled into the line. By a receiving device, radiation that has emerged from the line through a leak is received, as a result of which the leak becomes detectable.

2 Claims, 2 Drawing Sheets

FOREIGN PATENT DOCUMENTS

| | | |
|---|---|---|
| JP | 2001298252 A | 10/2001 |
| JP | 2002021582 A | 1/2002 |
| JP | 2003205899 A | 7/2003 |
| RU | 46579 U1 | 7/2005 |

\* cited by examiner

VALVE FOR A LEAK DETECTOR

This application is a continuation of U.S. patent application Ser. No. 12/083,759, filed Apr. 10, 2008 now issued as U.S. Pat. No. 7,921,694, which is a national stage application of the International Application No. PCT/EP2006/009822, filed on Oct. 11, 2006, both of which claim the benefit of the filing date of German Patent Application No. 10 2005 048 726.2 filed Oct. 12, 2005, the disclosures of which are hereby incorporated by reference.

The present invention relates to the general technical field of sensor technology. In particular, the present invention relates to a leak detector for detecting a leak in a line, to an arrangement for detecting a leak in a line, and to a method for detecting a leak in a line.

In many modern aircraft some pneumatic air is removed from the engines at determined positions. Using the air, which is commonly referred to as "bleed air", from the engines in this way avoids having to use a compressor. Generally speaking, such bleed air has a relatively high pressure (up to 50 PSI), and since it is taken from one of the compression stages of the engine it has a correspondingly high temperature of approximately 300° C. After being cooled to approximately 200 to 260° C., the air is made available to various consumers in the aircraft by way of lines. Among other things, bleed air is used for air conditioning and as service air.

To this effect the hot bleed air, which is under considerable pressure, has to be conveyed from the engines to the consumers by way of a pipeline system. In the case of a fault, for example in the case of a damaged pipe, this hot air emanates from the pipe at the location of the fault, where it can act directly on the surroundings. As a result of this, structural components of a cell or of a compartment, or some other sensitive components such as power lines, hydraulics or fuel lines, can be considerably heated up. Under some circumstances such considerable heating can have serious consequences in relation to the safety of the aircraft.

For this reason line sensors are presently known for detecting fractures or leaks in line systems or lines, which line sensors are installed along entire pipelines. Said line sensors comprise cylindrical lines, a few millimetres in thickness, comprising a core and a jacket.

There is a special material between the core and the jacket. The electrical resistance of this filler is very high in the case of temperatures that are below the response temperature. During the process of manufacturing the sheet-type sensors, the response temperature can be determined within certain limits.

However, the electrical resistance of the filler discontinuously increases by some decades when the response temperature has been exceeded. This change in resistance can be measured and detected by a system.

The sensors are installed along critical regions of the pipelines and are heated by the emanating hot air. When the response temperature has been reached, the leak is detected as a result of a change in resistance, and the air supply to the affected section is switched off by means of additional electronics.

In the past, leak detection was carried out by means of such sensor lines. However, for example an increasing use of temperature-sensitive plastics in aircraft engineering necessitates rapid switch-off of damaged pipeline sections. For this reason, today the requirements that have to be met are more stringent; they can only be met with difficulty by conventional technology.

From the time a leak occurs in a line, to the time this leak is detected, under certain circumstances a very long time may pass. Furthermore, if pipes are routed side by side, a fracture in one pipe might first activate the sensors of the other pipe so that consequently either the wrong pipeline or both pipelines have to be switched off.

It is an object of the present invention to provide a reliable system for detecting a leak in a line.

According to an exemplary embodiment of the invention a leak detector for detecting a leak in a line is provided. In this arrangement the leak detector comprises a transmitting device for generating radiation, and a receiving device. The generated radiation can be coupled into the line. The receiving device is designed to receive radiation that has emerged from the line through a leak, and consequently the leak becomes detectable.

According to another exemplary embodiment of the present invention an arrangement for detecting a leak in a line is provided, which arrangement comprises a leak detector with the characteristics described above, as well as a line.

According to yet another exemplary embodiment of the present invention, a method for detecting a leak in a line is provided, wherein, in the method, radiation is coupled into the line, and—in the case where there is a leak—by means of receiving the radiation that has emerged through the leaking position, the leak is detected.

According to an exemplary embodiment of the invention it is thus possible to detect a leak by means of radiation introduced into the line. The line can be a pipe, pipeline system or generally a line system. The radiation can be a physical quantity that differs from the material to be conveyed in the line. In this context the term material can in particular also refer to steam or hot air or to some other material to be conveyed. In other words a leak is not (only) detected by measuring the direct physically acting energy, for example the hot bleed air from an aircraft turbine. Instead, for detection, a process parameter is used that differs from the physically acting material, for example radiation by means of which a defective spot can be detected. In this way the process of detection can be decoupled from the process of conveying. It is thus possible to design and dimension the receiving device to detect this measuring process parameter, for example the radiation.

As a result of the above, the reaction of detection can be rendered independent of the substance that actually has to be conveyed. For example, the material to be conveyed might be a hot fluid. To be sure, leakage of fluid from a line, in particular a line pipe, can be detected by heating a sensor. However, this can result in a time delay between the leakage of the material and the detection of the material from the pipe, because, for example, a temperature sensor first has to be heated up to reach a particular temperature before a display or reaction can take place.

If in an advantageous manner, for example, radiation is used for detection, and thus the detection process is rendered independent of the substance that actually has to be conveyed, or its state of aggregation or material, the detection process can be accelerated. While in the case of detection via heating some time first passes until the sensor has heated up to trigger temperature, radiation such as electromagnetic waves, for example, can propagate at the speed of light, and in the case of leaking from a pipe can also be detected quickly.

Advantageously, with the use of radiation, a reaction time or the speed of detection of the leak that has occurred can be improved. Consequently, for example a faulty pipe can be switched off in time, before, for example, the bleed air emanating in an unwanted manner from the pipe causes damage to the surroundings.

According to a further exemplary embodiment of the present invention the receiving device is arranged outside the line. In this way radiation emanating from the pipe can be detected.

According to a further exemplary embodiment of the present invention, both the transmitting device and the receiving device are connected to an evaluation device. In this arrangement the evaluation device can control the transmission device; in particular, the evaluation device can determine the signal transmitted from the transmitting device. Furthermore, the evaluation device has information about the shape or the time sequence of the transmitted signal.

Since the evaluation device is also connected to the receiving device, the evaluation device can receive information about the signal received. It is thus possible to compare the transmitted signal with the received signal. With the use of particular coding forms or modulation forms it is thus possible to allocate a transmitted signal to a received signal and in this way to establish that the transmitted signal and the received signal belong together. This connection can be used to obtain information about the time response or the transit times of a signal transmitted into a line, until said signal reaches a receiving device, and said connection can be used to improve the reliability of the leak detector and to make it more resistant to operational errors.

Based on the transit times, taking into account the theoretical transit time of a signal in a line or in a region surrounding the line, information can be obtained about the location of a fault that has occurred. For maintenance purposes it can be advantageous if, based on the transit time, the location of a leak can be determined so as to better locate a fault or defective spot in a pipe. Consequently, an evaluation unit can not only be used to determine whether a leak has occurred in a line, but in addition, location of the defective spot can be made possible. Purely detecting the occurrence of a fault can be required in order to simply switch a faulty system off during the flight. Location of the defective spot is extremely useful for maintenance work.

According to a further exemplary embodiment of the present invention the radiation can be electromagnetic radiation (for example microwaves), acoustic radiation (for example ultrasound) or radioactive radiation (for example gamma radiation). Since in most cases the lines are used for conveying substances whose propagation depends on a flow speed, radiation can be a process parameter that can be detected well, whose propagation or propagation speed is however independent of the substance transported, or of the state of aggregation of said substance. As a rule, the flow speed of material is slower than the propagation speed of radiation. Advantageously, if radiation is used, measuring can take place while the material is being conveyed. However, measuring can also be carried out when the pipe is in an unused or in a dry state. The ability to detect faults without having to operate the actual system can in turn have advantages in the context of maintenance work.

In order to be able to detect leaks in a line system it is thus possible to prevent having to carry out the process for which the line is used as a distribution system. In order to detect any leakage in a line system or pipeline system for bleed air, it is thus possible to avoid having to operate the turbine from which the bleed air is taken. On the other hand it is no hindrance if the process of detection is carried out during operation of the actual material conveyance. It is thus possible to check the line for any leakages also while bleed air flows through the line.

According to a further exemplary embodiment of the present invention the evaluation device is connected to the receiving device by means of an electric bus. In this arrangement, with the use of a bus, an arrangement of several receivers along a line or pipe can be implemented.

Several receivers can be connected to each other by way of a bus line, and each receiver of the plurality of receivers can report a leak to the evaluation device, which can be arranged as a central evaluation device. In this way it is also possible to monitor extensive line systems.

According to yet another exemplary embodiment of the present invention an evaluation device can be connected to a receiving device or to a plurality of receiving devices, in each case by way of an individual connection. Because of the direct connection between the receiving device and the evaluation device, the evaluation device can establish an allocation to the respective receivers and to the signals transmitted by them. In this way it is, for example, possible to determine the location, in particular the region, of a leak. A receiver is often used to monitor a particular pipe section. By means of a receiver that is associated with a particular pipe section sending a signal to a central evaluation device, the central evaluation device can detect the faulty line region and switch it off in a targeted manner.

According to yet another exemplary embodiment of the present invention, the transmitting device can excite a mode in the line. In the context of this patent application the term "mode" can in particular refer to any wave shape determined by the geometry of the arrangement. The waves can be standing waves, which, when excited by corresponding excitation, form within the line. Using modes, the resonance behaviour of particular geometric structures with the interaction of physical excitation can be utilised for conveying information. While a mode is a standing wave within the conductor, the mode makes it possible to convey signals in a particular direction.

If the line is a pipe, and if the pipe has conductive properties, the pipe can be regarded as a hollow conductor for electromagnetic waves. In other words, from certain frequencies with which the signals are coupled into the hollow conductor, which frequencies are mostly in the HF (high-frequency) spectrum, standing electromagnetic waves form, which waves can, however, have a direction of propagation along the longitudinal direction of the pipe. With these waves, information can be distributed over the pipe. Such information distribution can essentially take place independently of the substance that is conveyed.

According to a further exemplary embodiment of the present invention the evaluation device is arranged for modulating a signal onto a carrier wave, and the modulated-on signal can be extracted, by the receiving device, from the received radiation. In concrete terms this means that a standing wave formed in a hollow conductor can transmit a signal that has been modulated onto this wave. To this effect the modulated-on signal can be modulated with high-frequency radiation, as a result of which the modulated-on signal can be transmitted.

The modulated-on signal receives a carrier wave that can have a higher frequency than the modulated signal. It is thus possible to determine a particular signal shape by modulation, while by mixing it with the carrier wave this modulated signal can be converted to a higher frequency range. In this context the term "mixing" can, in particular, designate a method, known from transmission technology, of increasing a signal of low frequency to a higher frequency range.

The higher frequency range can be in the magnitude of high-frequency radiation, i.e. for example ranging from 10 GHz to 20 GHz. A signal of such a high frequency can excite a corresponding mode in a line or pipe or hollow conductor, which mode makes it possible to achieve good transmission. In this context the term "good transmission" refers to transmission with the lowest possible attenuation.

In the context of electromagnetic waves, a distinction is made between the so-called transversal electrical (TE) and transversal magnetic (TM) and transversal electromagnetic (TEM) waves. Correspondingly there are associated modes. TE waves have no electrical component in the direction of propagation, while TM waves have no magnetic component in the direction of propagation. TEM waves are electromagnetic waves which, in the direction of propagation, have neither an electrical nor a magnetic component. With the use of suitable transmitters, corresponding waves can be excited. The mode that is excited within the line pipe depends on the respective frequency of the transmitter.

According to a further exemplary embodiment of the present invention the radiation used can be electromagnetic HF radiation.

According to a further exemplary embodiment of the present invention a low-frequency (LF) signal is modulated on the HF radiation. By modulating an LF signal on the HF radiation, the LF signal is transformed or folded to a higher frequency range. The frequency of the LF signal can be lower than the frequency required to excite a mode for propagating an electromagnetic wave in the line pipe. By means of modulating or mixing the LF signal on the HF radiation it is possible to achieve a situation wherein the LF signal is transformed to a frequency range in which a corresponding mode in the conductor can be excited. For example, a so-called $TE_{1,0}$ wave or a $TE_{1,0}$ mode, whose frequency is lowest, which wave or mode can be calculated for each pipe diameter, for example 6 inch, 8 inch or 9 inch, can be excited. The LF signal can thus be transmitted by way of a pipe section.

According to a further exemplary embodiment of the present invention the LF signal can be a sawtooth signal or a triangular signal. Sawtooth signals or triangular signals are easy to generate and are easy to recover. By means of the LF signal form determined by the evaluation device, a detected signal can easily be recognised again. Triangular modulation and sawtooth modulation are methods that are used in continuous wave frequency modulation (CWFM) radar technology as used in commercially available radar altimeters.

According to a further exemplary embodiment of the present invention the electromagnetic radiation can be a coded signal modulated onto electromagnetic HF radiation. The coded signal can, for example, be a pseudo-random function or pseudo noise (PN). This can make it possible to reduce the transmitting output while a signal can nevertheless be recognised again because by correlation the signal can be detected even in the noise. This arrangement uses a method that works with spread spectrum coding.

According to a further exemplary embodiment of the present invention the radiation can be pulsed. Pulsed radiation can require less energy than continuous radiation that is transmitted at constant energy. With the use of pulsed radiation, which is, for example, transmitted once per second, an adequate reaction time can be provided. Repeated pulsed radiation once per second can be adequate to meet the requirement of detecting a leak within seconds after it has been caused, and to react to such a leak.

According to a further exemplary embodiment of the present invention the receiving device can be an HF sensor. An HF sensor can be designed to detect high-frequency electromagnetic waves.

According to a further exemplary embodiment of the present invention the receiving device can be an antenna. An antenna can receive and evaluate HF radiation.

According to a further exemplary embodiment of the present invention the leak detector comprises a jacket element for encasing the line. Between the line and the jacket element the receiving device is arranged. The jacket element can insulate the line pipe, at the same time it can also be used for guiding radiation that has come out of the line pipe as a result of a leak. Without the jacket, the radiation could propagate freely into the space. Since a receiving device is arranged outside the line and since it is not possible to forecast the location of a leak, it may be advantageous to provide a device in the form of a jacket element that can lead leaked radiation in the direction of a receiving element. In this way it can be ensured that the radiation that is to be detected actually reaches the receiving device and provides the receiving device with adequate energy for detection.

A line monitored by a leak detector can be designed to guide a material flow. The term "material flow" also refers to steam or bleed air.

According to a further exemplary embodiment of the invention the line can be a pipe or a bleed air line. This line can either be completely made of electrically conductive material, or, if said line is not completely made of electrically conductive material, it can comprise a coating made of electrically conductive material. With the use of a coated material a hollow conductor can be defined in which an electromagnetic wave can propagate.

According to a further exemplary embodiment of the invention the line itself can be encased by electrically conductive material. In this way an electromagnetic wave in the external region, i.e. outside the line pipe of the line, can be conducted onward. In this arrangement the conductor can be an internal conductor, and the jacket can be an external conductor of a coaxial line. In a coaxial line, too, modes can be excited. Apart from high-frequency signals, low-frequency signals can also be transmitted by way of a coaxial line. In order to guide the radiation the jacket can be made from electrically conductive material or it can comprise an electrically conductive coating.

According to another embodiment a high-frequency method for continuous in-flight sensing of damage to a bleed air pipeline in an aircraft is created.

Many modifications of exemplary embodiments of the invention have been described with reference to the leak detector and the arrangement for detecting a leak in a line. These embodiments also apply to the method for detecting a leak in a line.

Below, exemplary embodiments of the present invention are described with reference to the figures.

In the following descriptions of FIGS. 1 to 4 the same reference characters are used for identical or corresponding elements.

Figure 1:
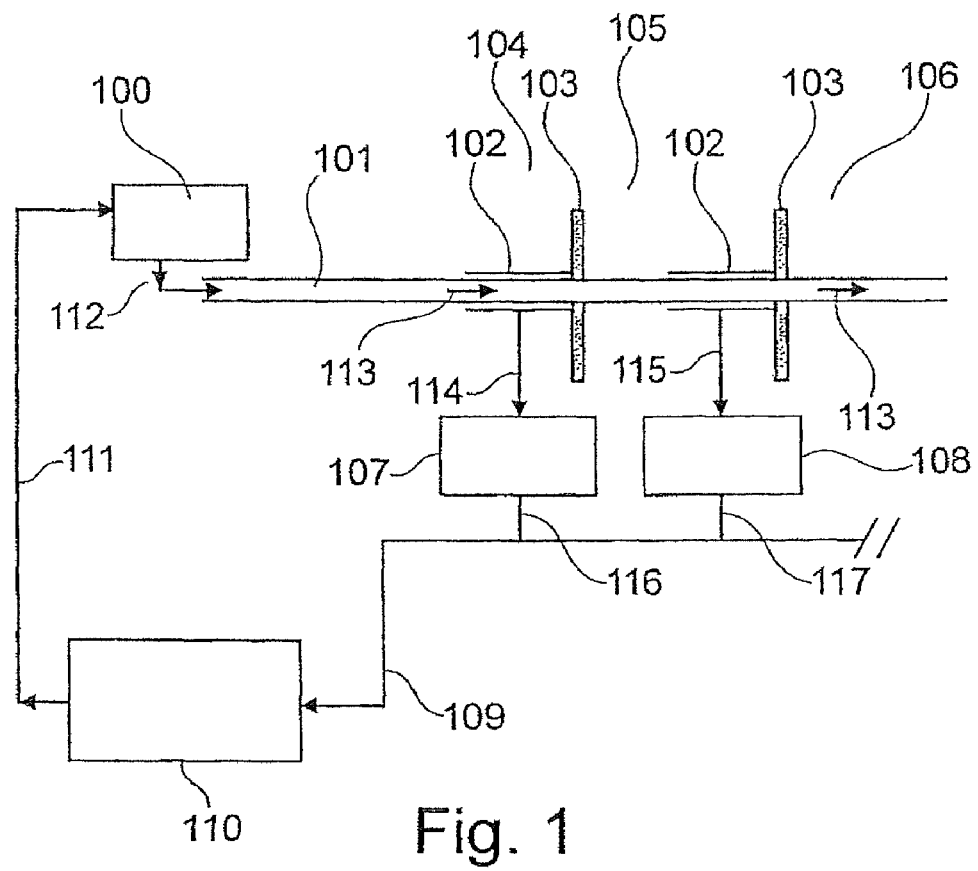
FIG. 1 shows a block diagram of an arrangement for detecting a leak in a line, according to an exemplary embodiment of the present invention.

FIG. 1 shows a block diagram of an arrangement for detecting a leak in a line. Reference character 101 shows a line. The material flow that propagates through the line is not shown in FIG. 1. The material flow is only indicated by the direction 113. The material flow can, for example, be bleed air that has been taken, for the purpose of on-board supply, from an engine. The line 101 is routed through structural components of the cell structure 103 of an aircraft. These supporting components, such as for example frames, ribs or stringers, are used for structural reinforcement of an aircraft component, such as for example a wing or fuselage. The structural components of the cell structure 103 divide three regions, the so-called compartments 104, 105, 106, through which the line 101 is routed. The arrangement of the line 101 and of the compartments 104, 105, 106 in FIG. 1 is symmetric, i.e. the line 101 is a round pipeline that is surrounded on all sides by the compartments 104, 105, 106.

The length of the compartments depends on the respective design; it can vary, for example ranging from 1 m to 5 m or 2.8 m to 10 m. The line itself is not interrupted by the structural parts of the cell structure 103. Only the external region of the line or of the line system 101 is divided into the compartments 104, 105, 106. The total length of the line 101 can, for example, range from 20 m to 50 m or from 40 m to 100 m. The line 101 is enclosed by the jacket 102. In FIG. 1 the jacket 102 encloses only part of the length of the line 101 that is routed in the compartments 104, 105, 106. However, the jacket 102 can also enclose the total length of the line 101, only being interrupted by the structural components of the cell structure 103.

In the compartments 104 and 105 two receivers 107 and 108 are arranged. The receivers 107, 108 are connected to the evaluation device 110 by way of the bus line 109. Although FIG. 1 only shows two receivers 107, 108, additional receivers may be connected to the bus line 109. There is an option (not shown in the diagram) of connecting each receiver 107, 108 directly to the central evaluation unit by way of an individual line.

The evaluation device 110 generates high-frequency radiation which it makes available to the transmitter 100 by way of the connection 111. The transmitter 100 couples the high-frequency radiation into the line 101 by way of the HF coupling device 112. The HF signal 111 can be a simple HF signal without modulation or an LF signal that has been modulated to HF radiation in the evaluation device. Furthermore, it is possible, by way of the connection 111 to provide an LF signal to the transmitter, and to carry out the mixing process in the transmitter 100.

Due to HF coupling of the transmitter into the line 101, HF radiation, shown by the arrows 113, propagates in the line 101, in the direction shown in FIG. 1, in the form of an electromagnetic wave. As long as the line 101 is tight, i.e. is not leaking, the HF radiation 113 within the line 101 is fed past the receivers 107, 108. The receivers do not receive any HF radiation.

If in either of the compartments 104 or 105 a leak or a defective spot in the line 101 occurs, the HF radiation 113 emerges from the line 101 and propagates between the jacket 102 and the line 101 in the direction 113 of the HF radiation, with such propagation taking place outside the line 101. Propagation from a compartment 104, 105 is stopped by the structural components of the cell structure 103. Consequently there are cell regions 104, 105, 106 in which there is a fault and thus electromagnetic HF radiation in the external region of the line pipe 101, and there are cell regions 104, 105, 106 where there is no HF radiation.

The HF receiver 107, 108 that is associated with the corresponding compartment 104, 105, 106 detects the presence of HF radiation, receives the HF signal by way of the HF inlet 114 or 115, evaluates said HF signal and by way of the LF line 116, 117 places a low-frequency (LF) signal on the bus 109.

The LF signal can either be a signal that the central evaluation device 110 has mixed onto HF radiation, or it can be a simple alarm signal. An alarm signal can only differentiate between the states of "HF detected" or "HF not detected". In other words an alarm signal places the bus to a defined potential so that the evaluation device 110, which can be centrally arranged, can only detect that somewhere on a receiver of the bus 109 a leak has been detected. The central evaluation device 110 can react accordingly.

The receivers 107, 108 can, for example, be strip conductors with Schottky diodes. If instead of the bus, each receiver 107, 108 is directly connected to the central evaluation device 110 by way of an individual line, conclusions can be drawn regarding the position of the fault, at least as to which compartment 104, 105, 106 is faulty.

The central evaluation device 110 detects the radiation of the given frequency. The size of the leakage can be estimated, by way of the amplitude of the received signal, in the central evaluation device 110. To this effect analogue to digital conversion of the amplitude of the received signal takes place in the receivers 107, 108. On the K bit, which is transmitted by the receivers 107, 108 to the central evaluation device 110 in the form of a binary signal, the central evaluation device 110 can estimate the size of the leakage.

The evaluation device 110 can modulate the transmission signal 111 in the time domain. Consequently the transmission output can be reduced because, as a result of a correlation carried out in the evaluation device 110, the signal can also be detected in the noise. By temporal modulation, the sensitivity of the arrangement is also increased, so that smaller leaks can also be detected. In the case of small leaks the output in the detected signal, which output is available outside the line 101, is low. In this arrangement small leaks relate to the frequency applied. This means that the leaks whose diameters are small in relation to the HF wavelength are designated small leaks. In small leaks little energy-rich HF radiation reaches the outside of the pipe 101.

With these signals of low energy, temporal modulation of the signal helps to improve the sensitivity of the arrangement, for example by coding, such as the use of pseudo-random frequency modulation or spread spectrum modulation.

In particular when the region between the jacket 102 and the line 101 is filled with insulating material, the propagation speeds both of the waves in the internal conductor 113 and in the space between the conductors 101 and 102 differ. Signal correlation in the evaluation device 110 helps to indirectly measure the location of damage. To this effect the transit time difference between the transmitter 100 and the receiver 107, 108 is measured and from it, in the case of known propagation speeds in the interior of the line 101 and in the space between the line 101 and the jacket 102, a conclusion is drawn as to the location where the pipe is damaged. To this effect an LF signal with a frequency ranging from 50 to 20,000 Hz is returned from the receivers 107, 108, with the use of individual lines (not shown in FIG. 1), to the evaluation device 110. In the evaluation device 110 the transmitted signal is compared to the received signal and is evaluated. A suitable modulation is for example a sawtooth modulation or triangular modulation as an LF signal, which is modulated with the HF transmission frequency with little swing.

Figure 2:
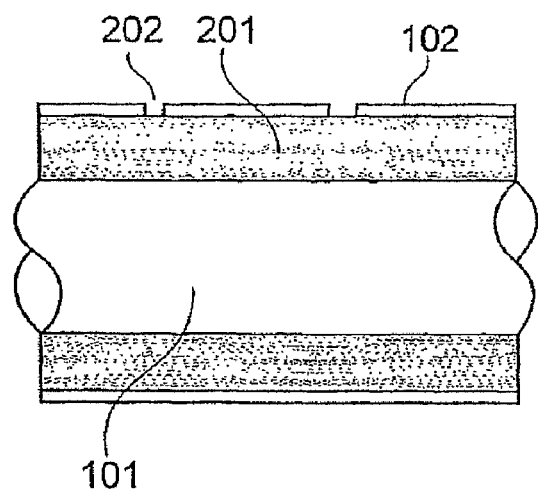
FIG. 2 shows a longitudinal section of a line pipe with a jacket according to an exemplary embodiment of the present invention.

FIG. 2 shows a longitudinal section of the line pipe 101 with a jacket 102. The longitudinal section shows that the jacket 102 essentially follows parallel to the alignment of the pipe 101. Insulation 201 is arranged between the jacket 102 and the line pipe 101. The pipe 101 comprises a conductive material, for example titanium or a titanium alloy. However, conductivity can also be achieved by using a coating with a non-conductive material that comprises a conductive coating. The thickness of the thermal insulation 201 ranges from 0.5 (0.01 m) to 2 inch (0.05 m). The thermal insulation comprises a non-conductive material, for example glass wool. The jacket 102 can be a thin conductive titanium foil that ranges in thickness from 0.5 to 3 mm. In addition, conventional temperature sensors can be installed on the holes 202, which are situated along the longitudinal axis, which holes can range from 0.5 to 2 mm in diameter. These conventional temperature sensors can be used to supplement the leak detector. However, the additional temperature sensors or temperature sensor lines are not essential.

Figure 3:
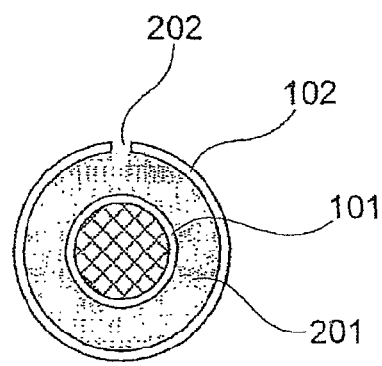
FIG. 3 shows a cross section of a further pipe with a jacket according to an exemplary embodiment of the present invention.

FIG. 3 shows the cross section of a pipeline according to FIG. 2. The pipeline or the internal pipe 101, comprises a diameter ranging from 6.5 inch (0.17 m) to 9 inch (0.23 m) or from 6 inches (0.15 m) to 8 inches (0.2 m). 6.5 inch and 9 inch are typical pipe diameters. Depending on the material selected, the wall strength of the pipe 101 ranges from 0.4 mm to 1 mm.

Figure 4:
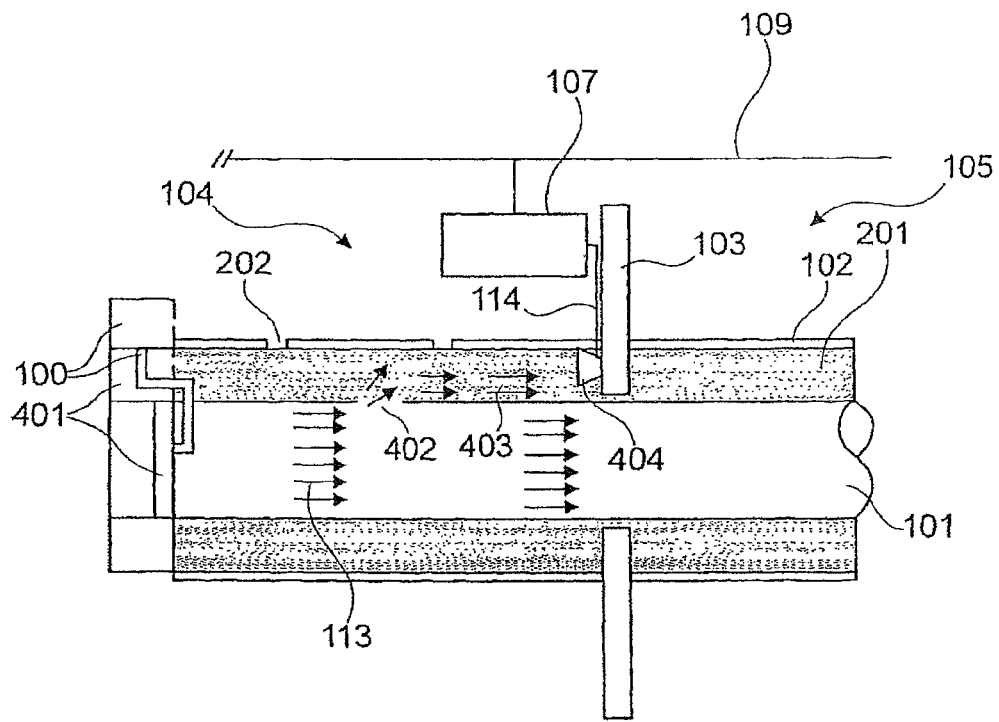
FIG. 4 shows a longitudinal section of a line pipe with a jacket and a receiving device, according to an exemplary embodiment of the present invention.

FIG. 4 shows a detailed longitudinal section of a line according to an exemplary embodiment of the present invention. FIG. 4 shows the line 101 which, by way of an electric or electropneumatic device 401, insulates a pipe region for the flow-through of material, such as for example bleed air. Insulation can for example be achieved by an electrically operated valve. By means of transmitters 100, in the internal pipe 101 an electromagnetic wave is coupled in, which wave moves in longitudinal direction away from the valve 401, parallel to the routing of the pipe. In this arrangement a thin conductor has been installed on the valve body made of metallic material. If required, the activation shaft of the valve can be used as such a coupling conductor.

FIG. 4 shows a leak 402 in the pipe wall of the line 101. The propagating mode of the HF radiation 113 can for example be a $TE_{1,0}$ mode of an electromagnetic wave. In the region of the damage or of the leak 402, part of the HF radiation 113 couples into the external region 201 between the line 101 and the jacket 102.

The electrically conductive line 101, together with the electrically conductive jacket 102, forms a coaxial line. Because of coupling due to the leak 402 in the coaxial conductor also, a mode of an electromagnetic wave 403 is excited. It extends, as an electromagnetic wave, between the external conductor 102 of the coaxial line and the internal conductor 101 of the coaxial line. The quality of the coupling 402 to the external region 201 depends on the size of the leakage 402 and on the frequency used for the HF radiation 113, as well as on the geometric data of both the line 101 and of the coaxial line 101, 102. The quality is a measure used in high-frequency technology, which measure allows conclusions relating to the quality of the coupling.

The higher the frequency of the HF radiation 113, the shorter the wavelength and the smaller the hole 402 that can be detected by means of such radiation. Because the interspace 201 corresponds to a coaxial conductor (internal conductor 101 and external conductor 102) there are no downward limitations in the frequency of the propagating waves. Therefore the losses during propagation of the coupled-in energy 403 are relatively low in this region. The waves propagate in the space until they eventually reach the aerial 404 and are conveyed to the receiver 107 by way of the line 114. From the received HF radiation the receiver 107 extracts an LF signal which, by way of the bus line or the individual line 109, it forwards for detection to an evaluation unit (not shown in FIG. 4).

The frame or rib 103 separates the two compartments 104 and 105. While in the region of the compartment 104 in which the leak 402 has occurred the HF radiation is carried away to the external region 201, in the external region 201 of the compartment 105 there is no HF radiation because in the region of the compartment 105 there is no leak. The aerial 404 that is used for receiving the HF radiation is arranged on the structural part of the cell structure 103. Said aerial 404 receives all the HF radiation that in the region of the compartment 104 reaches the external region 201.

Detection of the HF radiation can essentially take place as soon as the leak 402 occurs, because the speed of detection depends only on the speed of propagation of the electromagnetic wave in the line 101 and in the space 201. Propagation of the electromagnetic waves takes place almost at the speed of light.

In concrete terms this means that to achieve detection it is not necessary, for example, for the compartment 104 to first be heated to a certain temperature, because leakages are not detected by heating a sensor, i.e. they are not detected by measuring the energy that has a physical effect. Consequently, quick reporting of the damage can be made possible. The leakage is not detected by the heating of a sensor, i.e. by measuring the energy that has a physical effect; instead, a defect in the internal pipe 101 is detected as a result of electromagnetic coupling. Consequently, immediate damage reporting is possible.

Since the leaking HF radiation 403 is guided in the internal region 201 as a result of the coaxial conduction effect of the external conductor 102 and the internal conductor 101, influencing a parallel arrangement for leak detection, or the influence of a leaking pipe that is arranged in parallel can be prevented, as a result of which a safe reaction to a fault can be made possible. Any damage sustained on one pipe will not lead to erroneous detection on the undamaged pipe that is routed parallel to the damaged pipe, which thus makes it possible to reliably react to a fault.

Since the energy is coupled into the entire hollow space and can therefore largely be measured independently of the actual place of installation of the receiver, the position of the damage is not particularly important. The position of the damage is thus not particularly important because the energy is coupled into the entire hollow space or compartment, and measuring can therefore be undertaken largely independently of the concrete place of installation of the receiver. In the case of sensors known today, in order to make possible rapid detection, the jet of hot air must directly reach the sensor by emerging through the holes in the insulation 202. Depending on the damage sustained, reaching a sensor directly is not always possible.

Since detection does not depend on the material conveyed but instead takes place by means of an additionally applied process parameter, a leak can also be detected when the pipe is not in use.

It is not necessary for the emerging air to reach the sensors as accurately as possible in order to ensure a fast response by the sensors.

If pipes are routed side-by-side, as is the case in the wing of the A380, a situation can be prevented where a fracture in a pipe first activates the sensors of the other pipe, with corresponding incorrect isolating measures, or where both sensors are activated, as a result of which both pipeline systems have to be switched off. A situation can be prevented where, should the emerging air not reach the sensors directly, first the entire surroundings have to be heated to the response temperature before a leakage can be detected, which could lead to considerable local damage.

Below, the design of a modern pipeline is described, as shown in FIGS. 2 and 3. At its core is the actual pipe 101, which is made from titanium or a titanium alloy. Such pipes exist in various diameters, for example in 6.5 inch (0.17 m) and 9 inch (0.23 m). Depending on the material used, the wall thickness ranges from 0.4 mm to 1 mm. Thermal insulation 201 approximately 1 inch (0.025 m) in thickness is placed around the pipe. Said thermal insulation comprises a non-conductive material, for example glass wool. A thin conductive titanium foil 102 provides a cover towards the outside. Along the longitudinal axis there are small holes 202 in the titanium foil, which holes 202 are several mm in thickness, above which holes 202 the temperature sensor line is usually routed.

FIG. 4 again shows the above pipeline. On the left-hand side there is the electric (or electro-pneumatic) device 401 to isolate the pipe section that follows on to the right-hand side, with such isolation taking place for example by an electrically operating valve. Reference character 103 in FIG. 4 indicates that time and again the insulation/jacket of the pipe has to be interrupted in those positions in which the pipe leads through structural components of the cell structure 103.

Exemplary embodiments of the present invention may provide that the internal conductor may be used as an electrical hollow conductor for conveying transversal electrical (TE) or transversal magnetic (TM) waves. To this effect the valve 401 is modified. A thin conductor 100 is installed on the valve body (usually made of metal); however, if required the activation shaft of the valve can be used as such a coupling conductor. This conductor is fed with high frequency current from a transmitter 100, which is arranged near the valve 401. The frequency of the transmitter 100 is selected such that with a known pipe diameter of the line 101 unattenuated propagation results. One option is the so-called TE1.0 wave, whose frequency is lowest; wherein said frequency can be calculated for each diameter (6 inch (0.15 m), 8 inch (0.2 m), 9 inch (0.23 m), etc.).

Since the internal pipe is routed from the source right up to the consumer without any opening towards the outside, the advancing electromagnetic wave stays within the internal pipe. Therefore, in the normal case there is never any measurable HF radiation in the insulation layer 201. In this very insulation layer 201, which forms the hollow space between the internal conductor 101 and the metal insulation 102, HF sensors 107, 108 are arranged at critical positions.

Typically, in front of every interruption in the outer jacket, for example as a result of leadthroughs 103, one such detector 107, 108 and a receiver must be in place. The output signal can be a simple alarm signal (HF detected, not detected) or it can be an LF signal (demodulation of signal impressions for locating purposes). Interconnection can take place, for example, by way of a bus system 109 or by way of individual wiring (not shown).

If, in the case of a fault, the internal pipe 402 is damaged, then the internal conductor 101 couples some of the HF radiation 403 in the space 201. In this arrangement the quality of the coupling essentially depends on the form and size of the damage. Because the interspace 201 corresponds to a coaxial conductor (internal conductor and external conductor) there are no downward limitations in the frequency of the propagating waves. Therefore the losses during propagation of the coupled-in energy 403 are relatively low in this region. These waves propagate in the interspace until they eventually reach the receivers 107, 108 and are detected. Said receivers 107, 108 acknowledge receipt and in this way register the pipe damage 402.

In the simplest form an electrical replacement connection diagram as shown in FIG. 1 results. Central evaluation 110 controls the transmitter 100, which in the case shown couples regulated-output constant-time radiation of defined frequencies into the internal pipe. At dedicated positions 103 in the interspace the receiver circuits 107, 108 are arranged. The output signals are transmitted for central evaluation by way of a bus 109 or by way of individual lines. In the present case, evaluation consists of pure detection of radiation of the given frequency, perhaps in addition with imprecise differentiation of the amplitude (k bit) in order to roughly estimate the extent of the leakage.

In an expanded form the sender signal can be modulated over time. On the one hand, in this way it is possible to significantly reduce the transmission output because the signal can be detected by correlation even in the noise (compare for example GPS technology). Moreover, the sensitivity of the arrangement is greatly improved so that even smaller leaks can be detected.

On the other hand, generally speaking, the propagation speeds of the waves in the internal conductor and in the interspace differ significantly. Signal correlation can therefore help to indirectly measure the location of damage. To this effect the transit time difference between the transmitter and the receiver is measured, and from it, in the case of known propagation speeds in the internal pipe and in the interspace, conclusions are drawn in relation to the location of pipe damage. Generally speaking, the output signal of the receivers is an LF signal (50 . . . 20,000 Hz) that has to be switched onward with the corresponding quality for central evaluation. There the actual assessment takes place.

For example sawtooth modulation or triangular modulation of the transmission frequency with little swing is a suitable modulation. This is known CWFM radar technology as used in commercially available radar altimeters. Also imaginable is pseudo-random frequency modulation, as used in GPS technology.

In addition it should be pointed out that "comprising" does not exclude other elements or steps, and "a" or "one" does not exclude a plural number. Furthermore, it should be pointed out that characteristics or steps which have been described with reference to one of the above exemplary embodiments can also be used in combination with other characteristics or steps of other exemplary embodiments described above. Reference characters in the claims are not to be interpreted as limitations.

The invention claimed is:

1. A valve for a leak detector, the valve comprising:
   a valve body; and
   a conductor;
   wherein the conductor is installed on the valve body;
   wherein the valve is adapted to insulate a pipe region for the flow-through of material; and
   wherein the conductor is adapted to couple an electromagnetic wave in a pipe such that the electromagnetic wave moves in a longitudinal direction away from the valve.

2. The valve of claim 1, further comprising an activation shaft, wherein the activation shaft of the valve is configured to be used as the coupling conductor.

* * * * *